US012716099B2

(12) United States Patent
Brockman et al.

(10) Patent No.: US 12,716,099 B2
(45) Date of Patent: Aug. 25, 2026

(54) IDENTIFYING DEFECTS IN CANINE NUCLEOTIDE SALVAGE PATHWAYS AND COMPOSITIONS AND METHODS FOR IMPROVING IMMUNE FUNCTION IN DOGS

(71) Applicant: Hill's Pet Nutrition, Inc., Topeka, KS (US)

(72) Inventors: Jeffrey Brockman, Lawrence, KS (US); Matthew Jackson, Topeka, KS (US)

(73) Assignee: Hill's Pet Nutrition, Inc., Overland Park, KS (US)

(*) Notice: Subject to any disclaimer, the term of this patent is extended or adjusted under 35 U.S.C. 154(b) by 874 days.

(21) Appl. No.: 18/050,486

(22) Filed: Oct. 28, 2022

(65) Prior Publication Data

US 2023/0193391 A1 Jun. 22, 2023

Related U.S. Application Data

(60) Provisional application No. 63/265,625, filed on Dec. 17, 2021.

(51) Int. Cl.

*C12Q 1/6883* (2018.01)
*A23K 20/142* (2016.01)
*A23K 50/40* (2016.01)

(52) U.S. Cl.

CPC .......... *C12Q 1/6883* (2013.01); *A23K 20/142* (2016.05); *A23K 50/40* (2016.05); *C12Q 2600/156* (2013.01)

(58) Field of Classification Search

None

See application file for complete search history.

(56) References Cited

U.S. PATENT DOCUMENTS

2021/0186059 A1 6/2021 Brockman et al.

FOREIGN PATENT DOCUMENTS

WO 2023/069411 4/2023

OTHER PUBLICATIONS

Russo et al Progress in Nutrition. 2019. 21(4): 965-970 (Year: 2019).*

Leeb et al "A Missense Variant Affecting the C-Terminal Tail of UNC93B1 in Dogs with Exfoliative Cutaneous Lupus Erythematosus (ECLE)" Genes. Feb. 3, 2020. 11(159): p. 1-10 and Supplemental Table S3, 56 pages total (Year: 2020).*

International Search Report and the Written Opinion of the International Searching Authority issued in International Application PCT/US2022/078833 mailed Feb. 14, 2023.

Choi et al, 2012, "A deficiency in nucleoside salvage impairs murine lymphocyte development, homeostasis, and survival," J. Immunology 188(8):3920-7.

* cited by examiner

*Primary Examiner* — Carla J Myers

(57) ABSTRACT

Methods of identifying a dog as having deficient nucleic base salvage and methods of identifying a dog as being at an elevated risk and increased likelihood of developing immune dysfunction are disclosed. Methods of treating a dog to prevent, delay onset of or reduce severity of symptoms of immune dysfunction in the dog and methods of treating a dog diagnosed with or suspected of having immune dysfunction are disclosed. Methods of treating a dog diagnosed with or suspected of having immune dysfunction are disclosed. The disclosed methods include performing a genetic analysis of the dog to detect the presence of 2 copies of major allele G for single nucleotide polymorphism Affx-205876096. Nutritionally complete and balanced dog food compositions are disclosed. The nutritionally complete and balanced dog food compositions comprise a therapeutic level of nucleotides.

16 Claims, 6 Drawing Sheets

Specification includes a Sequence Listing.

uridine + phosphate uracil + ribose 1-phosphate

Intake Nucelotides (g/kg BW^0.75)

Quantiles

| | | |
|---|---|---|
| 100.0% | maximum | 0.0278579809 |
| 99.5% | | 0.0274005747 |
| 97.5% | | 0.0254502612 |
| 90.0% | | 0.0224830083 |
| 75.0% | quartile | 0.020548634 |
| 50.0% | median | 0.0190616236 |
| 25.0% | quartile | 0.0175856289 |
| 10.0% | | 0.0150903623 |
| 2.5% | | 0.0131496913 |
| 0.5% | | 0.0038685656 |
| 0.0% | minimum | 0.0001058142 |

Summay Statistics

| | |
|---|---|
| Mean | 0.0190671 |
| Std Dev | 0.0030984 |
| Std Err Mean | 0.0001005 |
| Upper 99% Mean | 0.0193264 |
| Lower 99% Mean | 0.0188077 |
| N | 951 |

SEQUENCE LISTING

```
Sequence total quantity: 1
SEQ ID NO: 1            moltype = DNA  length = 201
FEATURE                 Location/Qualifiers
source                  1..201
                        mol_type = genomic DNA
                        organism = Canis sp.
SEQUENCE: 1
cagtttaaaa cttttgctaa tattttttgc ataaattgaa attcataata ttatacattt  60
attattttgt atcgtttagg taaaactgtg taattttaac rtttagctta gtagtcttaa  120
cagaaaattt aaaataatca gactgaattt tcttatttta taaattttgc tactatttat  180
acataattag catgataatg t                                            201
```

IDENTIFYING DEFECTS IN CANINE NUCLEOTIDE SALVAGE PATHWAYS AND COMPOSITIONS AND METHODS FOR IMPROVING IMMUNE FUNCTION IN DOGS

CROSS-REFERENCE TO RELATED APPLICATION

This application claims the benefit of U.S. Provisional Application No. 63/265,625, filed Dec. 17, 2021, which is incorporated by reference herein in its entirety.

REFERENCE TO AN ELECTRONIC SEQUENCE LISTING

The application contains a Sequence Listing which has been submitted electronically in XML format. The contents of the electronic sequence listing Named: 13108-00-US-01-HL_SEQ_Listing_ST26.xml; Size: 2027 bytes; and Date of Creation: Sep. 14, 2022, is herein incorporated by reference in its entirety.

BACKGROUND

A large pool of nucleic bases is required for DNA replication in dividing cells and transcription of DNA into RNA for basic cell function. The de novo synthesis of nucleic bases requires a large consumption of cellular energy. To reduce this energy requirement, organisms have evolved methods for salvaging nucleic bases from DNA and RNA degradation to help maintain the overall nucleic bases pools. Degradation of DNA or RNA results in the liberation of nucleosides. In order for the organism to salvage and reuse the purine and pyrimidine bases without new de novo synthesis the sugar must be removed from the nucleic base of the nucleoside.

The two main types of nucleic acids, DNA and RNA, are polymers made from nucleotides, which are the monomeric units of the polymer. Each nucleotide contains a five-carbon sugar backbone, a phosphate group, and a nitrogen base. The phosphate group and the nitrogen base are linked to the sugar backbone at different carbons of the sugar. The sugar in DNA is deoxyribose; the sugar in RNA is ribose. The phosphate group of one nucleotide forms a bond with the sugar of another nucleotide. The sugars are linked together in series by phosphate bridges form a sugar phosphate backbone of a DNA or RNA polymer; each sugar of the sugar phosphate backbone has a nucleic base attached.

There are four possible nucleic bases included in DNA: adenine, guanine, cytosine and thymine. There are four possible nucleic bases in RNA: adenine, guanine, cytosine and uracil. Adenine and guanine each have a single nitrogen containing ring and are called purines; cytosine, thymidine and uracil each have two nitrogen containing rings and are called pyrimidines.

A nucleoside is a nucleotide without the phosphate group; that is, a nucleoside is a nucleic base linked to a sugar (deoxyribose or ribose) via a β-N1-glycosidic bond. Adenine when linked to 2-deoxyribose is deoxyadenosine and when linked to ribose is adenosine. Guanine when linked to 2-deoxyribose is deoxyguanosine and when linked to ribose is guanosine. Cytosine when linked to 2-deoxyribose is deoxycytidine and when linked to ribose is cytidine. Thymine when linked to 2-deoxyribose is deoxythymidine. Uracil when linked to ribose is uridine (symbol U or Urd). Although not used in DNA, uracil occurs linked to deoxyribose and is referred to as deoxyuridine. Deoxyuridine can occur by removal of an amino group from cytosine resulting in uracil. Deoxyuridine also occurs non-intentionally from deoxyuridine monophosphate (dUMP), which is the deoxygenated form of uridine monophosphate (UMP), and the precursor to deoxythymidine monophosphate (dTMP), a component of DNA nucleotide biosynthesis.

Nucleic bases can be synthesized de novo to provide the building blocks of nucleic acids which are need for cell function and replication. In addition, nucleic bases can be recovered from the degradation process of nucleic bases by a nucleic bases salvage process. A deficiency in nucleic bases salvage has a negative impact on lymphocyte development in mice. Deficiencies in the nucleic base salvage pathway in a dog increase the risk and likelihood of immune dysfunction.

BRIEF SUMMARY

The presence of 2 copies of the major allele of the single nucleotide polymorphisms Affx-205876096 or a single nucleotide polymorphism (SNP) in linkage disequilibrium therewith in a dog subject is associated with a defect in the pyrimidine salvage pathway and the increased risk and likelihood of immune dysfunction. The methods comprise the step of analyzing a biological sample obtained from the dog for the presence of 2 copies of major allele G for single nucleotide polymorphism Affx-205876096 or a single nucleotide polymorphism in linkage disequilibrium thereof in the dog. The presence of 2 copies of major allele G for single nucleotide polymorphism Affx-205876096 indicates that the dog has a defect or deficiency in nucleic base salvage. The dog is administered a complete nutritional diet that comprises a therapeutic level of nucleotides, wherein the complete nutritional diet is a complete and balanced nutritional dog food that comprises 0.055-0.075% nucleotides on a dry matter basis.

Methods of identifying a dog as having deficient nucleic base salvage are provided. The methods comprise the step of analyzing a biological sample obtained from the dog for the presence of 2 copies of major allele G for single nucleotide polymorphism Affx-205876096 or a single nucleotide polymorphism in linkage disequilibrium thereof in the dog. The presence of 2 copies of major allele G for single nucleotide polymorphism Affx-205876096 indicates that the dog has a defect or deficiency in nucleic base salvage.

Methods of identifying a dog as being at an elevated risk and increased likelihood of developing immune dysfunction are provided. The methods comprise the step of analyzing a biological sample obtained from the dog for the presence of 2 copies of major allele G for single nucleotide polymorphism Affx-205876096 or a single nucleotide polymorphism in linkage disequilibrium thereof in the dog. The presence of 2 copies of major allele G for single nucleotide polymorphism Affx-205876096 indicates that the dog has an elevated risk and increased likelihood of developing immune dysfunction within its lifetime.

Methods of treating a dog to prevent, delay onset of or reduce severity of symptoms of immune dysfunction in a dog are provided. The methods comprise the steps of identifying the dog as having an elevated risk and increased likelihood of developing immune dysfunction by analyzing a biological sample obtained from the dog for the presence of 2 copies of major allele G for single nucleotide polymorphism Affx-205876096 or a single nucleotide polymorphism in linkage disequilibrium thereof in the dog. The presence of 2 copies of major allele G for single nucleotide polymorphism Affx-205876096 indicates that the dog has an elevated risk and increased likelihood of developing immune dysfunction within its lifetime. The dog is administered a complete nutritional diet that comprises a therapeutic level of nucleotides. The complete nutritional diet is a complete and balanced nutritional dog food that comprises 0.055-0.075% nucleotides on a dry matter basis. In some embodiments, the dog is monitored for the onset of immune dysfunction symptoms regularly after being identified as being an increased risk and likelihood of immune dysfunction.

Methods of treating a dog who has been diagnosed with or suspected of having immune dysfunction are provided. The methods comprise identifying the dog as a dog diagnosed with or suspected of having immune dysfunction and identifying the dog as having a defect or deficiency in nucleic base salvage. The dog is identified as a dog as having a defect or deficiency in nucleic base salvage by analyzing a biological sample obtained from the dog for the presence of 2 copies of major allele G for single nucleotide polymorphism Affx-205876096 or a single nucleotide polymorphism in linkage disequilibrium thereof in the dog. The presence of 2 copies of major allele G for single nucleotide polymorphism Affx-205876096 indicates that the dog has a defect or deficiency in nucleic base salvage.

The methods provided herein may further comprise the additional step of measuring the serum level of uridine and/or deoxyuridine or both in the dog and comparing the level measured to a standard indicative a level in dogs with a normal nucleic base salvage process.

Nutritionally complete and balanced dog food compositions are provided. The nutritionally complete and balanced dog food compositions comprise a therapeutic level of nucleotides, wherein the therapeutic level of nucleotides comprises 0.055-0.075% nucleotides on a dry matter basis.

DETAILED DESCRIPTION

Figure 1:
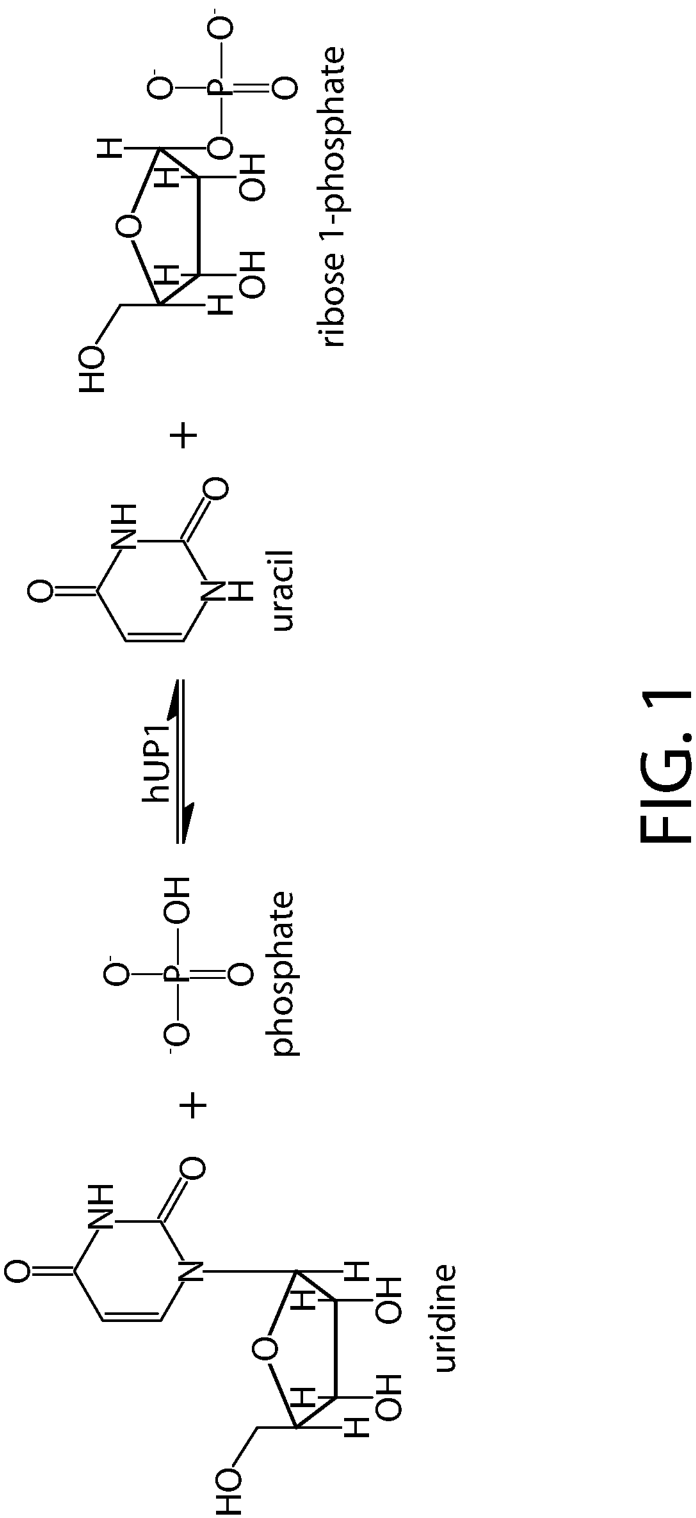
FIG. 1 depicts the hUP1 reaction converting uridine and phosphate into uracil and ribose 1phosphate.

The following description of the preferred embodiment(s) is merely exemplary in nature and is in no way intended to limit the invention, its application, or uses.

As used herein and in the appended claims, the singular forms “a”, “an”, and “the” include plural reference unless the context clearly dictates otherwise.

The term “dog” is synonymous with the term “canine” and includes male and female canines including *Canis familiaris*.

A “food,” “food composition,” “pet food composition” or “dog food composition” can, in some embodiments, be a nutritionally complete diet for the dog to which it is fed.

“Daily nutritional intake” and “total nutritional intake per day” refer to dry matter intake per day. That is, water weight is not included in calculating the amount of nutrition consumed per day. To the extent that food and food ingredient contain water/moisture, the dry matter represents everything in the sample other than water including protein, fiber, fat, minerals, etc. Dry matter weight is the total weight minus the weight of any water. Dry matter intake per day is calculated as the total nutritional intake per day excluding all water. For example, an amount of an ingredient equal to a specific percent of daily nutritional intake refers to the amount of that ingredient in dry matter form (i.e., excluding all water) relative to the total amount of dry matter consumed (also excluding all water) in a day. The skilled artisan would readily recognize and understand nutritional amounts and percentages expressed as dry matter amounts, dry matter weights and dry matter percentages. Since foods, whether wet, moist or dry, generally contain as certain amount of water, when calculating daily dry matter intake, the water component of such food is excluded. To calculate total daily nutritional intake, which is dry matter intake per day, water is excluded. To calculate percent of an ingredient of total daily intake on a dry matter basis, water is removed from the total intake to give total daily dry matter intake and the percent of the ingredient is based on amount of ingredient present as dry matter.

As used herein, an “ingredient” refers to any component of a composition.

As used herein, the term “treatment” refers to eliminating or alleviating or ameliorating, or preventing or delaying onset or reducing the severity of one or more symptoms.

The term “nutrient” refers to a substance that provides nourishment. In some cases, an ingredient may comprise more than one “nutrient,” for example, a composition may comprise corn comprising important nutrients including both protein and carbohydrate.

Food compositions can be provided to in the form of dog food. A variety of commonly known types of dog foods are available to dog owners. The selection of dog food includes but is not limited to wet dog food, semi-moist dog food, dry dog food and dog treats. Wet dog food generally has a moisture content greater than about 65%. Semi-moist dog food typically has a moisture content between about 20% and about 65% and may include humectants, potassium sorbate, and other ingredients to prevent microbial growth (bacteria and mold). Dry dog food such as but not limited to food kibbles generally has a moisture content below about 15%. Pet treats typically may be semi-moist, chewable treats; dry treats in any number of forms, or baked, extruded or stamped treats; confection treats; or other kinds of treats as is known to one skilled in the art.

As used herein, the term “kibble” or “food kibble” refers to a particulate pellet like component of dog foods. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term “kibble” or “food kibble” is used, it can refer to an uncoated kibble or a coated kibble.

As used herein, the term “extrude” or “extrusion” refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced dog food compositions. A "nutritionally complete diet" is a diet that includes sufficient nutrients for maintenance of normal health of a healthy dog on the diet. Nutritionally complete and balanced dog food compositions are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like.

As described herein, increased or elevated likelihood or risk of developing immune dysfunction refers to having a greater than average chance that an individual dog will develop immune dysfunction compared to that of a dog that has a heterozygous genotype of the major alleles for the specific SNPs discussed herein.

Methods of identifying dogs that have a defective and deficient nucleic base salvage pathways and a reduced ability of salvaging nucleotides are provided.

Methods of mitigating the risk of certain conditions as a result by supplementation of nucleotides are provided.

Compositions for and methods of treating dogs that have defect in the nucleotide salvage pathways are provided including reagents and kits that may be used in such methods. Compositions for and methods of preventing, reducing the severity and/or delaying the onset of immune dysfunction in dogs identified as being at increased risk of immune dysfunction are provided including reagents and kits that may be used in such methods. Compositions for and methods for improving immune function in dogs identified as being at increased risk of immune dysfunction are provided including reagents and kits that may be used in such methods. Reagents, kits and methods for evaluating the genetic makeup of a dog are provided for identifying dogs that have defect in the nucleotide salvage pathways. Reagents, kits and methods for evaluating the genetic makeup of a dog are provided for identifying dogs that are at increased risk of immune dysfunction.

Methods provided include methods that comprise determining which dogs may have a reduced ability of salvaging nucleotides and a method of mitigating the risk of certain conditions as a result of a reduced ability of salvaging nucleotides by dietary supplementation with nucleotides is provided.

Overview

Single nucleotide polymorphisms (SNPs), a common type of genetic variation, are single base pair mutations at a specific locus. That is, a SNP is a difference in a single nucleotide in a DNA sequence that occurs at a specific position in a genome. Typically, for a SNP at a specific position, there are two possible nucleic base variations, which are referred to as alleles for that position. Within a population, the nucleic base variation that most commonly appears at a specific base position in a genome is referred to as the major allele; the nucleic base variation that is less common at that specific base position is referred to as the minor allele. Canines, like most multicellular organisms have two sets of chromosomes. Thus, each dog has two copies of each gene or locus and therefore two copies of each SNP. Accordingly, for each SNP in the dog's genome, the dog may have two copies of the major allele, or one copy of the major allele and one copy of the minor allele, or two copies of the minor allele. When a particular allele occurs disproportionately among individuals with a disease or condition relative to its occurrence in a broader population, SNPs can act as biological markers for elevated risk or increased likelihood of developing that disease or condition. SNP genotyping refers to identification of the alleles of a SNP present within the genome. There are numerous methods for detecting SNPs, interrogating SNPs and performing SNP genotyping.

Genetic analysis reveals a genetic marker for a deficiency in a nucleic base salvage pathway causing a reduced ability of salvaging nucleotides in dogs. Nucleic base salvage complements de novo nucleic base synthesis, which is an requires significantly more energy that nucleic base salvage. The less nucleic base salvage function available thereby requires greater reliance on de novo nucleic base synthesis. Negative effects of this reliance can occur when dogs are under stress, such as when a dog is suffering from infection, cancer, autoimmune disease or chronic inflammation. In stress situations, the greater reliance on the high energy requirement de novo nucleic base synthesis can negatively impact and impair immune function.

Reliance on the high energy requirement de novo nucleic base synthesis may have a negative impact on lymphocyte development. Lymphocytes make up about 20-40% of circulating white blood cells and include Natural Killer Cells, T cells and B cells, which each serve critical functions in the immune system. Accordingly, a negative impact on lymphocyte development may have a negative impact on immune function. Nucleic base salvage pathways are therefore critical to the maintenance of the immune system and a deficiency in nucleic base salvage may lead to immune dysfunction. Deficiencies in the nucleic base salvage pathway in a dog elevate the risk and increase likelihood of immune dysfunction.

The genetic marker for a deficiency in nucleic base salvage is a homozygous major allele GG (the GG haplotype) at single nucleotide polymorphism (SNP) Affx-205876096, which is on canine chromosome 18 upstream from the UPP1 gene that encodes for Uridine phosphorylase (UP), an enzyme in the nucleic base salvage pathway. During the DNA/RNA degradation processes, the DNA or RNA is broken down into constituent nucleosides which are further processed to remove the sugar from the nucleic base. The nucleosides uridine and 2-deoxy uridine are processed by UP to remove the sugar from the nucleic base. UP uses phosphate and uridine or 2-deoxyuridine as substrates to produce uracil and ribose-1-phosphate or deoxyribose-1-phosphate, respectively. That is:

Processing of Uridine to Uracil by Uridine phosphorylase (FIG. 1)

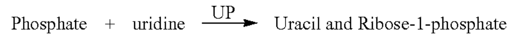

Processing of 2-deoxy uridine to Uracil by UP

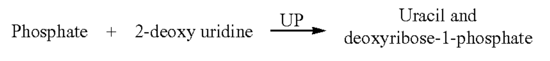

Uracil and ribose-1-phosphate are substrates that are used by the enzyme Uridine phosphoribosyl transferase reform the nucleotide Uridine monophosphate (UMP). That is:

Conversion of Uracil and Ribose-1-phosphate to Uridine monophosphate by Uridine phosphoribosyl transferase

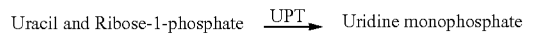

The UMP then enters the normal nucleotide pathways for RNA, DNA, and other metabolic processes.

Dogs homozygous for the G major allele have increased levels of Uridine and 2-deoxy-Uridine in serum indicating that individuals with two copies of the G allele are less efficient at converting the nucleosides Uridine to the nucleic base Uracil and ribose-1-phosphate and the nucleoside 2-deobxy-Urindine to Uracil and deoxyribose-1-phosphate by uridine phosphorylase which in turn can limit the amount of UMP generated by the pyrimidine salvage pathway. Less efficient production of UMP by the nucleic base salvage pathway requires more de novo nucleotide synthesis which imposes an increased energy burden.

Dogs with the genetic marker for deficient nucleic base salvage are more reliant on de novo nucleotide synthesis. Given that a large percentage of dogs are homozygous for the G allele, it is unlikely that this variant results in a clinical manifestation under normal circumstances. However, when an individual with this genotype is under stress such as an infection, cancer, autoimmune condition, or chronic inflammation, the deficiency in nucleic base salvage and consequent higher reliance on de novo nucleotide synthesis may negatively impact lymphocyte development. Dogs with the genetic marker for deficient nucleic base salvage have an elevated risk and higher likelihood to develop immune dysfunction, and accordingly, the genetic marker for deficient nucleic base salvage is the genetic marker for elevated risk and higher likelihood of immune dysfunction. Mitigating the negative impact of the deficient nucleic base salvage may reduce the risk and likelihood of developing an immune dysfunction as well as prevent, delay the onset, reduce severity and otherwise treat immune dysfunction and its symptoms.

Dogs with the genetic marker for elevated risk and higher likelihood of immune dysfunction may benefit from dietary supplementation of nucleotides that can replenish the normal nucleotide levels without putting an additional energy burden of de novo nucleotide synthesis. To this end diet has been designed for dogs with the GG genotype, particularly when under immune stress. The diet, which contains a therapeutic level of nucleotides, helps to maintain the normal pools of nucleotides and deliver optimum nutrition for an individual dog's specific need given its genetic background at this locus and clinical condition.

Dogs with genetic marker for a deficiency in nucleic base salvage and an elevated risk and higher likelihood of immune dysfunction can be identified by analyzing a biological sample of a dog to determine the genotype of the dog at SNP Affx-205876096, i.e., whether the dog has the GG haplotype for SNP Affx-205876096. Dogs with genetic marker are likely to benefit from being fed a diet having a therapeutic level of nucleotides as described herein. Dogs that have been identified as having the genetic marker for a deficiency in nucleic base salvage and an elevated risk and higher likelihood of immune dysfunction are identified as being likely to benefit from a diet having a therapeutic level of nucleotides as described herein. Dogs that have been identified as having the genetic marker but do not have observable clinical symptoms of immune dysfunction may be subject of monitoring methods in which the dog is monitored more closely for such symptoms or indicators of immune dysfunction so that therapeutic intervention can be initiated early. Dogs that are diagnosed with or suspected of having immune dysfunction and that have been identified as having the genetic marker are identified as being likely to benefit from a diet having a therapeutic level of nucleotides as described herein.

Monitoring methods may include more regular and/or frequent testing and examinations then are typically scheduled for a dog at the age and health status of the dog being monitored. Monitoring may include blood analysis for the presence and level of uridine and deoxy-uridine in serum. Monitoring may include blood analysis for the presence and level of blood cells which develop from lymphocytes such lymphoid progenitor cells and myeloid progenitor cells and the cells that develop therefrom. Blood analysis for the presence and level of cells derived from lymphoid progenitor cells include B lymphocytes including plasma cells derived therefrom; T lymphocytes including helper ($CD4^+$) T cells, regulatory T cells and cytotoxic ($CD8^+$) T cells; NK T cells and NK cells. Blood analysis for the presence and level of cells derived from myeloid progenitor cells include monocytes including monocyte-derived macrophage and dendritic cells; neutrophils, basophils eosinophils and mast cells. Blood analysis can also be undertaken to monitor cytokine and chemokine levels. Monitoring may include examinations and testing for symptoms and diagnostic indicators of conditions and diseases involving the immune system including those due to improper regulation such as allergy and autoimmune disease as well as those indicating deficiency in immune responses such as indicators of an immunocompromised condition, chronic infection and inability to clear an infection.

Methods of treating a dog to prevent, delay onset of, and reduce severity of symptoms of immune dysfunction in dogs having a deficiency in nucleic base salvage and an elevated risk and higher likelihood of immune dysfunction include the steps of identifying the dog as such by analyzing a biological sample obtained from the dog to determine the genotype of the dog at SNP Affx-205876096, i.e., whether the dogs has the GG haplotype for SNP Affx-205876096 and feeding dogs so identified with a diet having nucleotides as described herein. The nucleotides may be incorporated in the food at treatment levels as part of a nutritionally complete and balanced dog food composition or added in the form of an additive supplement to an otherwise nutritionally complete and balanced dog food composition.

Methods of treating a dog diagnosed with or suspected of having immune dysfunction include the steps of identifying the dog as having a deficiency in nucleic base salvage and an elevated risk and higher likelihood of immune dysfunction by analyzing a biological sample obtained from the dog to determine the genotype of the dog at SNP Affx-205876096 as being homozygous major allele G, i.e., whether the dogs has the GG haplotype for SNP Affx-205876096, and feeding dogs so identified with a diet having nucleotides as described herein. The nucleotides may be incorporated in the food at treatment levels as part of a nutritionally complete and balanced dog food composition or added in the form of an additive supplement to an otherwise nutritionally complete and balanced dog food composition. Methods may comprise additional steps of diagnosing the dog with or observing indicators supporting the suspicion that the dog has immune dysfunction in prior to or after determining whether the dog has the GG haplotype for SNP Affx-205876096.

Monitoring methods as described above may be undertaken to monitor progression of disease or response to therapy in dogs diagnosed with or suspected of having immune dysfunction and identified as being homozygous major allele G, i.e., whether the dog has the GG haplotype for SNP Affx-205876096, and treated by feeding dogs so identified with a diet having therapeutic levels of nucleotides as described herein. The various testing and examination results prior to feeding can be compared to testing and examination results subsequent to initiating the high nucleotide feeding treatment.

Each of the methods set forth include identifying the dog as being homozygous for major allele G, i.e., identifying the dog as having the GG haplotype for SNP Affx-205876096, by genetic analysis (genotyping) of a biological sample obtained from the dog including: methods of identifying a dog as having a deficiency in nucleic base salvage; methods of identifying a dog as having an elevated risk and higher likelihood of immune dysfunction; methods of identifying a dog as likely to benefit from being fed a diet having nucleotides; methods of monitoring a dog with no observable clinical symptoms of immune dysfunction and identified as having the genetic marker for a deficiency in nucleic base salvage and an elevated risk and higher likelihood of immune dysfunction; methods of identifying a dog diagnosed with or suspected of having immune dysfunction as being likely to benefit from a diet having therapeutic levels of nucleotides; methods of treating a dog to prevent, delay onset of, and reduce severity of symptoms of immune dysfunction; methods of treating a dog diagnosed with or suspected of having immune dysfunction; and methods of monitoring progression of disease or response to therapy in dogs diagnosed with or suspected of having immune dysfunction and being treated by feeding with a diet having therapeutic levels of nucleotides. There are numerous different methods to determine a genotype at a SNP. As provided herein, these methods may be used to interrogate a biological sample obtains from the dog to determine whether the dog has the GG haplotype for SNP Affx-205876096. Reagents, kits and methods that include identifying a dog that has the GG haplotype for SNP Affx-205876096 are provided. In addition, compositions and methods are provided for treating dogs identified a as having the GG haplotype for SNP Affx-205876096.

In such methods, a biological sample from the dog is obtained. In some embodiments, the sample is a genomic DNA sample. In some embodiments, the sample is obtained from blood, saliva, follicle root, nasal swab or oral swab of the canine subject. Some embodiments comprise the step of collecting the biological sample from the dog. In some embodiments, a biological sample obtained from the dog is a biological sample that has been received subsequent to collection. In some embodiments, the biological sample is a genomic DNA sample from the dog using the commercially available kit such as PERFORMAgene PG-100 Oral sample collection (DNA Genotek, OraSure Technologies, Inc., Bethlehem, PA).

Identifying the dog as having the GG haplotype for SNP Affx-205876096, by genetic analysis (genotyping) of a biological sample obtained from the dog can be accomplished by any of several well-established genotyping methodologies.

In some embodiments, the GG haplotype for SNP Affx-205876096 may be detected using methods that include at least one nucleic acid analysis technique selected from: DNA sequencing, restriction enzyme digest, polymerase chain reaction (PCR), hybridization, real-time PCR, reverse transcriptase PCR, or ligase chain reaction.

In some embodiments, the GG haplotype for SNP Affx-205876096 may be detected by performing at least one nucleic acid analysis technique selected from the group consisting of: analysis using a whole genome SNP chip; single-stranded conformational polymorphism (SSCP) assay; restriction fragment length polymorphism (RFLP); automated fluorescent sequencing; clamped denaturing gel electrophoresis (CDGE); denaturing gradient gel electrophoresis (DGGE); mobility shift analysis; restriction enzyme analysis; heteroduplex analysis; chemical mismatch cleavage (CMC); RNase protection assays; use of polypeptides that recognize nucleotide mismatches; allele-specific PCR; sequence analysis; and SNP genotyping.

In some embodiments, the GG haplotype for SNP Affx-205876096 may be detected using a method selected from the types of methods consisting of: hybridization-based methods, enzyme-based methods, post-amplification methods based on physical properties of DNA, and sequencing methods.

In some embodiments, the GG haplotype for SNP Affx-205876096 may be detected using a method selected from the types of methods consisting of: hybridization-based methods selected from the group consisting of: dynamic allele-specific hybridization, molecular beacon methods and SNP microarrays; enzyme-based methods selected from the group consisting of: restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of: single strand conformation polymorphism, temperature gradient gel electrophoresis, denaturing high performance liquid chromatography, high-resolution amplicon melting, DNA mismatch-binding proteins, SNPlex™, and surveyor nuclease assay; and sequencing methods In some embodiments, the GG haplotype for SNP Affx-205876096 may be detected using a low-density array.

In some embodiments, the GG haplotype for SNP Affx-205876096 may be detected using a high-density array containing genetic markers. Examples of arrays include the commercially available microarrays.

In some embodiments, the MassARRAY™ System is used in the detection of the presence of the GG haplotype for SNP Affx-205876096. The MassARRAY™ System is a non-fluorescent detection platform utilizing mass spectrometry to accurately measure PCR-derived amplicons. Mass spectrometry, coupled with end point PCR, enables highly multiplexed reactions under universal cycling conditions to provide accurate, rapid, and cost-effective analysis. The MassARRAY™ System offers a unique solution for targeted genetic testing with limited input material.

In some embodiments, bead array technology is used in the detection of the GG haplotype for SNP Affx-205876096. For example, the Illumina™ BeadArray technology and the Infinium™ HD assay (Illumina, Inc. San Diego, CA) may be used. The Illumina™ BeadArray technology is based on small silica beads that self-assemble in microwells on planar silica slides. Each bead is covered with hundreds of thousands of copies of a specific oligonucleotide that act as a capture sequence in the Infinium™ assay. Once the beads have self-assembled, a proprietary decoding process maps the location of every bead, ensuring that each one is individually quality controlled. The result of this manufacturing process is that every BeadChip undergoes rigorous testing to assure the highest possible quality standards. The Infinium assay can be scaled to unlimited multiplexing without compromising data quality, unlike many alternative PCR-dependent assays. The simple streamlined workflow is common across all products, no matter how many SNPs are being interrogated. Likewise, the data acquisition process and analysis are the same. The Infinium assay protocol features single-tube sample preparation and whole genome amplification without PCR or ligation steps significantly reducing labor and sample handling errors. After hybridizing unlabeled DNA samples on the Beadchip, two-step allele detection provides high call rates and accuracy. Selectivity and specificity are accomplished in two-steps. Target hybridization to bead-bound 50-mer oligos provides high selectivity while enzymatical single-base extension also incorporates a labeled nucleotide for assay readout. The staining reagent is optimized to provide a higher signal, and more balanced intensities between red and green channels. These features contribute to accuracy, high call rates and copy number data with low noise. The Infinium assay produces two-color readouts (one color for each allele) for each SNP in a genotyping study including SNP Affx-205876096. Intensity values for each two-color channels, A and B, convey information about the allelic ratio at a single genomic locus. Typical studies incorporate values for a large number of samples (hundreds to tens of thousands) to ensure significant statistical representation. When these values are appropriately normalized and plotted distinct patterns (or clusters) emerge, in which samples have identical genotypes at an assayed locus exhibit similar signal profiles (A and B values) and aggregate in clusters. For diploid organisms, bi-allelic loci are expected to exhibit three clusters (AA, AB and BB). Genotype calls are based upon information derived from standard cluster file, which provides statistical data from a representative sample set. This enables genotypes to be called by referencing assay single intensities against known data for a given locus. Since the call accuracy is tied to the quality of the cluster data, having efficient and robust clustering algorithm is essential for accurate genotyping. The Illumina™ Gebtrain2 algorithm accurately and efficiently identifies cluster pattern of genotyping samples and reports summary.

The GG haplotype for SNP Affx-205876096 may be detected using hybridization-based methods. Examples of hybridization-based methods include dynamic allele-specific hybridization, methods that employ molecular beacons, and methods that employ SNP microarrays including high-density oligonucleotide SNP arrays or low-density oligonucleotide SNP arrays. SNPs can be interrogated by hybridizing complementary DNA probes to the SNP site. In dynamic allele-specific hybridization, a genomic segment is amplified and attached to a bead through a PCR reaction with a biotinylated primer. The amplified product is then attached to a streptavidin column and washed to remove the unbiotinylated strand. An allele-specific oligonucleotide is then added in the presence of a molecule that fluoresces when bound to double-stranded DNA. The intensity is measured as temperature is increased until the melting temperature (Tm) can be determined. SNP are detected by their lower-than-expected Tm. Specifically engineered single-stranded oligonucleotide probes are used in SNP detection that uses molecular beacons. Oligonucleotides are designed in which complementary regions are at each end and a probe sequence is located in between such that the probes take on a hairpin, or stem-loop, structure in its natural, isolated state. A fluorophore is attached to one end of the probe a fluorescence quencher is attached to the other end. The fluorophore is in close proximity to the quencher when the oligo is in a hairpin configuration and the molecule does not emit fluorescence. The probe sequence is complementary to the genomic DNA used in the assay. If the probe sequence of the molecular beacon encounters its target genomic DNA during the assay, it will anneal and hybridize. The oligo will no longer assume the hairpin configuration and will fluoresce. High-density oligonucleotide SNP arrays comprise hundreds of thousands of probes arrayed on a small chip, allowing for many SNPs to be interrogated simultaneously. Several redundant probes designed to have the SNP site in several different locations as well as containing mismatches to the SNP allele are used to interrogate each SNP. The differential amount of hybridization of the target DNA to each of these redundant probes, allows for specific homozygous and heterozygous alleles to be determined.

The GG haplotype for SNP Affx-205876096 may be detected using enzyme-based methods. A broad range of enzymes including DNA ligase, DNA polymerase and nucleases may be employed. Examples of enzyme-based methods include methods based upon restriction fragment length polymorphism (RFLP), PCR-based methods, methods that utilize Flap endonuclease; methods that utilize primer extension, methods that utilize 5'-nuclease and methods that include oligonucleotide ligation assays. RFLP methods to detect SNPs use many different restriction endonucleases to digestion a genomic sample. It is possible to ascertain whether or not the enzymes cut the expected restriction sites by determining fragment lengths through a gel assay. RFLP assays are designed to include enzymes that cut in the presence or absence of SNPs and the pattern of fragment lengths can be used to determine the presence or absence of SNPs. PCR based methods include tetra-primer amplification refractory mutation system PCR, or ARMS-PCR, and multiple qPCR reactions. Tetra-primer amplification refractory mutation system PCR, or ARMS-PCR, employs two pairs of primers to amplify two alleles in one PCR reaction. The primers are designed such that the two primer pairs overlap at a SNP location but each match perfectly to only one of the possible SNPs. Alternatively, multiple qPCR reactions can be run with different primer sets that target each allele separately. Some embodiments utilize Flap endonuclease (FEN), which is an endonuclease that catalyzes structure-specific cleavage. This cleavage is highly sensitive to mismatches and can be used to interrogate SNPs with a high degree of specificity. A FEN called cleavase is combined with two specific oligonucleotide probes, that together with the target DNA, can form a tripartite structure recognized by cleavase. The first probe, called the Invader oligonucleotide is complementary to the 3' end of the target DNA. The last base of the Invader oligonucleotide is a non-matching base that overlaps the SNP nucleotide in the target DNA. The second probe is an allele-specific probe which is complementary to the 5' end of the target DNA, but also extends past the 3' side of the SNP nucleotide. The allele-specific probe will contain a base complementary to the SNP nucleotide.

Primer extension is a two-step process that first involves the hybridization of a probe to the bases immediately upstream of the SNP nucleotide followed by a 'mini-sequencing' reaction, in which DNA polymerase extends the hybridized primer by adding a base that is complementary to the SNP nucleotide. This incorporated base is detected and determines the SNP allele. The primer extension method is used in a number of assay formats. These formats use a wide range of detection techniques that include MALDI-TOF Mass spectrometry (see Sequenom) and ELISA-like methods. Sequenom's iPLEX SNP™ genotyping method, which uses a MassARRAY™ mass spectrometer. The flexibility and specificity of primer extension make it amenable to high throughput analysis. Primer extension probes can be arrayed on slides allowing for many SNPs to be genotyped at once. Referred to as arrayed primer extension (APEX), this technology has several benefits over methods based on differential hybridization of probes.

Illumina Incorporated's Infinium assay is an example of a whole-genome genotyping pipeline that is based on primer extension method. In the Infinium assay, over 100,000 SNPs can be genotyped. The assay uses hapten-labelled nucleotides in a primer extension reaction. The hapten label is recognized by antibodies, which in turn are coupled to a detectable signal. APEX-2 is an arrayed primer extension genotyping method which is able to identify hundreds of SNPs or mutations in parallel using efficient homogeneous multiplex PCR (up to 640-plex) and four-color single-base extension on a microarray. The multiplex PCR requires two oligonucleotides per SNP/mutation generating amplicons that contain the tested base pair. Methods that utilize 5'-nuclease include methods using Taq DNA polymerase's 5'-nuclease activity in the TaqMan assay for SNP genotyping. The TaqMan assay is performed concurrently with a PCR reaction and the results can be read in real-time as the PCR reaction proceeds. In methods that include oligonucleotide ligation assays, oligonucleotide DNA ligase catalyzes the ligation of the 3' end of a DNA fragment to the 5' end of a directly adjacent DNA fragment. This mechanism can be used to interrogate a SNP by hybridizing two probes directly over the SNP polymorphic site, whereby ligation can occur if the probes are identical to the target DNA. Examples of other post-amplification methods for detecting SNPs include methods based upon DNA's physical properties. Such methods first involve PCR amplification of the target DNA.

Several methods of genotyping SNPs are based upon DNA's physical properties such as melting temperature and single stranded conformation. Methods that use single stranded conformation are based upon single-stranded DNA (ssDNA) that folds into a tertiary structure. The conformation is sequence dependent and most single base pair mutations will alter the shape of the structure. When applied to a gel, the tertiary shape will determine the mobility of the ssDNA, providing a mechanism to differentiate between SNP alleles. This method first involves PCR amplification of the target DNA. The double-stranded PCR products are denatured using heat and formaldehyde to produce ssDNA. The ssDNA is applied to a non-denaturing electrophoresis gel and allowed to fold into a tertiary structure. Differences in DNA sequence will alter the tertiary conformation and be detected as a difference in the ssDNA strand mobility. Temperature gradient gel electrophoresis (TGGE) or temperature gradient capillary electrophoresis (TGCE) methods are based on the principle that partially denatured DNA is more restricted and travels slower in a gel or other porous material. In another method, denaturing high performance liquid chromatography (DHPLC) uses reversed-phase HPLC to interrogate SNPs. In DHPLC, the solid phase which has differential affinity for single and double-stranded DNA. Another method used is high-resolution melting of the entire amplicon. Use of DNA mismatch-binding proteins may also be used to detect SNPs. MutS protein from *Thermus aquaticus* binds different single nucleotide mismatches with different affinities and can be used in capillary electrophoresis to differentiate all six sets of mismatches. SNPlex™ is a proprietary genotyping platform sold by Applied Biosystems. Surveyor nuclease assay uses surveyor nuclease, a mismatch endonuclease enzyme that recognizes all base substitutions and small insertions/deletions (indels), and cleaves the 3' side of mismatched sites in both DNA strands. Sequencing technologies can also be used in SNP detection. Advances in sequencing technology allow SNP genotyping by sequencing more practical.

Genotyping by sequencing using next generation sequencing technologies has become a common practice. Genotyping by sequencing, also called GBS, is a method to discover single nucleotide polymorphisms (SNP) in order to perform genotyping studies, such as genome-wide association studies (GWAS). GBS uses restriction enzymes to reduce genome complexity and genotype multiple DNA samples. After digestion, PCR is performed to increase the fragment pool and then GBS libraries are sequenced using next generation sequencing technologies. With the advancement of next generation sequencing technologies such as Illumina short read sequencing by synthesis and PacBio's single molecule real time sequencing it is becoming more feasible to do GBS. In the future, development of new technologies such as nanopore single molecule sequencing may allow whole genome sequencing/genotyping.

Treatment

The treatments used to reduce the risk and likelihood of developing immune dysfunction in a dog identified as having an elevated risk and increased likelihood or risk of developing immune dysfunction by the detection of the GG haplotype for SNP Affx-205876096 and the treatments used to eliminate, alleviate, ameliorate or reduce severity of symptoms of immune dysfunction in dogs diagnosed with or suspected of having immune dysfunction and identified as having deficient nucleic base salvage by detection of the GG haplotype for SNP Affx-205876096 comprise feeding the dog a nutritionally complete diet that comprises a therapeutic level of nucleotides as described herein.

Treatment methods are provided to prevent, delay onset and/or reduce severity of immune dysfunction in dogs identified as having deficient nucleic base salvage in dogs. The GG haplotype for SNP Affx-205876096 indicates deficient nucleic base salvage in dogs. Dogs with the GG haplotype for SNP Affx-205876096 have an elevated risk and increased likelihood of developing immune dysfunction. Treatment methods to prevent, delay onset and/or reduce severity of immune dysfunction in dogs comprises the method of identifying the dog as having the GG haplotype for SNP Affx-205876096. The GG haplotype for SNP Affx-205876096 is detected in a biological sample obtained from the dog. The dog is fed a nutritionally complete diet that comprises a therapeutic level of nucleotides.

Treatment methods are provided to eliminate or alleviate or ameliorate, or reduce the severity of one or more symptoms of immune dysfunction in a dog diagnosed with or suspected of having immune dysfunction and identified as having the GG haplotype for SNP Affx-205876096. The GG haplotype for SNP Affx-205876096 is detected in a biological sample obtained from the dog. The dog is fed a nutritionally complete diet that comprises diet that comprises a therapeutic level of nucleotides.

A nutritionally complete diet that comprises a therapeutic level of nucleotides is a nutritionally complete diet that comprises 0.055-0.075% nucleotides on a dry matter basis. In some embodiments, the dog is fed a nutritionally complete diet that comprises a therapeutic level of nucleotides wherein the dog is fed a nutritionally complete diet that comprises 0.055%, 0.056%, 0.057%, 0.058%, 0.059%, 0.060%, 0.061%, 0.062%, 0.063%, 0.064%, 0.065%, 0.066%, 0.067%, 0.068%, 0.069%, 0.070%, 0.071%, 0.072%, 0.073%, 0.074% or 0.075% nucleotides on a dry matter basis. In some embodiments, the dog is fed a nutritionally complete diet that comprises a therapeutic level of nucleotides wherein the dog is fed a nutritionally complete diet that comprises 0.056-0.074% nucleotides on a dry matter basis. In some embodiments, the dog is fed a nutritionally complete diet that comprises a therapeutic level of nucleotides wherein the dog is fed a nutritionally complete diet that comprises 0.057-0.073% nucleotides on a dry matter basis. In some embodiments, the dog is fed a nutritionally complete diet that comprises a therapeutic level of nucleotides wherein the dog is fed a nutritionally complete diet that comprises 0.058-0.072% nucleotides on a dry matter basis. In some embodiments, the dog is fed a nutritionally complete diet that comprises a therapeutic level of nucleotides wherein the dog is fed a nutritionally complete diet that comprises 0.059-0.071% nucleotides on a dry matter basis. In some embodiments, the dog is fed a nutritionally complete diet that comprises a therapeutic level of nucleotides wherein the dog is fed a nutritionally complete diet that comprises 0.060-0.070% nucleotides on a dry matter basis. In some embodiments, the dog is fed a nutritionally complete diet that comprises a therapeutic level of nucleotides wherein the dog is fed a nutritionally complete diet that comprises 0.061-0.069% nucleotides on a dry matter basis. In some embodiments, the dog is fed a nutritionally complete diet that comprises a therapeutic level of nucleotides wherein the dog is fed a nutritionally complete diet that comprises 0.062-0.068% nucleotides on a dry matter basis. In some embodiments, the dog is fed a nutritionally complete diet that comprises a therapeutic level of nucleotides wherein the dog is fed a nutritionally complete diet that comprises 0.063-0.067% nucleotides on a dry matter basis. In some embodiments, the dog is fed a nutritionally complete diet that comprises a therapeutic level of nucleotides wherein the dog is fed a nutritionally complete diet that comprises 0.062-0.066% nucleotides on a dry matter basis. In some embodiments, the dog is fed a nutritionally complete diet that comprises a therapeutic level of nucleotides wherein the dog is fed a nutritionally complete diet that comprises 0.063-0.065% nucleotides on a dry matter basis. In some embodiments, the dog is fed a nutritionally complete diet that comprises a therapeutic level of nucleotides wherein the dog is fed a nutritionally complete diet that comprises 0.064% nucleotides on a dry matter basis.

Compositions and Formulations

Application of the methodology outlined above comprise feeding a dog a nutritionally complete diet that comprises a therapeutic level of nucleotides. The food product is a nutritionally complete diet for a canine having a specified age and weight.

The compositions include food compositions is suitable for consumption by a companion animal, particularly a dog, that a therapeutic level of nucleotides compositions and may additionally comprise protein in an amount from 4% to 75% or more based on the total weight of the composition on a dry matter basis, fat in an amount from 5% to 50% or more based on the total weight of the composition on a dry matter basis, and carbohydrate from 5% to 75% or more based on the total weight of the composition on a dry matter basis, wherein the food composition is suitable for consumption by a dog.

In some embodiments, the compositions include food compositions is suitable for consumption by a companion animal, particularly a dog, that a therapeutic level of nucleotides in combination with protein and/or fat and/or carbohydrate. In some embodiments, for example, in addition to a therapeutic level of nucleotides, a nutritionally complete diet is a nutritionally complete and balanced dog food composition that may comprise: from 4% to 90%, from 4% to 75%, from 5% to 75%, from 10% to 60% protein, or from 15% to 50% by weight of protein based on the total weight of the composition on a dry matter basis; from 0% to 90%, from 2% to 80%, from 5% to 75%, and from 10% to 50% by weight of carbohydrate based on the total weight of the composition on a dry matter basis; and from 2% to 60%, from 5% to 50%, and from 10% to 35% by weight of fat based on the total weight of the composition on a dry matter basis. In some embodiments, for example, in addition to a therapeutic level of nucleotides, a nutritionally complete diet is a nutritionally complete and balanced dog food composition that may further contain from 0 to 15% or from 2% to 8%, by weight of other vitamins, and minerals, antioxidants, and other nutrients, e.g., amino acids which support the nutritional needs of the animal.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

In some embodiments, proteins useful as ingredients of the food compositions may comprise proteins from animal sources, such as animal proteins, including mammalian, avian protein, reptilian, amphibian, fish, invertebrate proteins and combinations thereof; e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as soy protein isolate, corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, Perna canaliculata, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids such as but not limited to lauric acid, myristic acid, palmitic acid, palmitoleic acid, margaric acid, margaroleic acid, stearic acid, oleic acid, linoleic acid, g-linolenic acid, α-linolenic acid, stearidonic acid, arachidic acid, gadoleic acid, DHGLA, arachidonic acid, eicosatetraenoic acid, EPA, behenic acid, erucic acid, docosatetraenoic acid, and DPA.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises one or more other vitamins, such as but not limited to vitamin A, vitamin C, vitamin D, vitamin E, quinoa grain, thiamine, riboflavin, niacin, pyridoxine, pantothenic acid, folic acid, vitamin B12, biotin, and choline.

In some embodiments, the food composition further comprises fiber, which may be supplied from a variety of sources, including, for example, vegetable fiber sources such as cellulose, beet pulp, peanut hulls, and soy fiber.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry matter basis of the composition).

In some embodiments, compositions, foods, and diets comprise chicken in an amount from 5% to 25% based on the total weight of the composition on a dry matter basis. In certain embodiments, compositions comprise chicken in an amount of 5%, 7.5%, 10%, 12.5%, 15%, 17.5%, 20%, 22.5% or 25% based on the total weight of the composition on a dry matter basis In some embodiments, compositions, foods, and diets comprise egg protein in an amount from 4% to 15% based on the total weight of the composition on a dry matter basis. In certain embodiments, compositions comprise egg protein in an amount of 4%, 5%, 6%, 7%, 8%, 9%, 10%, 11%, 12%, 13%, 14% or 15% based on the total weight of the composition on a dry matter basis.

In some embodiments, compositions, foods, and diets comprise corn gluten meal in an amount from 6% to 20% based on the total weight of the composition on a dry matter basis. In certain embodiments, compositions comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis.

In some embodiments, compositions, foods, and diets comprise carrots, spinach, tomato pomace, and combinations thereof, in an amount from 0.5% to 2% based on the total weight of the composition on a dry matter basis. In certain embodiments, compositions comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis.

In certain embodiments, compositions comprise a fruit source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis.

In certain embodiments, compositions comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis.

In another aspect of this embodiment, the food comprises from 5% to 50% carbohydrate, by dry weight of the composition, selected from millet, brewers rice, oat groats, and combinations thereof.

Preparation of Compositions

A nutritionally complete diet may be a nutritionally complete and balanced dog food composition that comprises a therapeutic level of nucleotides and may be prepared as food products suitable for consumption by dogs. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist food products generally have a moisture content of from 25% to 35%. The food products may also include components of more than one consistency, for example, soft, chewy meat-like particles or pieces as well as kibble having an outer cereal component or coating and an inner "cream" component.

In some embodiments, the food products that comprise a therapeutic level of nucleotides may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using conventional processes known to those of ordinary skill in the art. Typically, dry ingredients, including dried animal protein, plant protein, grains and the like are ground and mixed together. Liquid or moist ingredients, including fats, oils, water, animal protein, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between species and breeds of animals, as well as one of more of the attributes of the animal. For example, cat foods, for example, are typically formulated based upon the life stage, age, size, weight, body composition, and breed.

In another embodiment, treats comprising therapeutic levels of nucleic bases can be prepared by, for example, an extrusion or baking process similar to those described below for dry food to provide an edible product. Treats include, for example, compositions that are given to an animal to entice the animal to eat during a non-meal time. Treats may be nutritional, wherein the composition comprises one or more nutrients, and may, for example, have a composition as described above for food. Non-nutritional treats encompass any other treats that are non-toxic. Compositions can be coated onto the treat, incorporated into the treat, or both.

In another embodiment, an animal toy is provided that is a chewable or consumable toy. Such toys are typically prepared by coating any existing toy with therapeutic levels of nucleic bases. Toys therefore include, for example, chewable toys. Contemplated toys for cats include, for example, artificial bones. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable toys (e.g., toys comprising plastic components) and fully consumable toys (e.g., rawhides and various artificial bones).

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

A cohort of ~900 dogs were genotyped using the Affymetrix Canine High Density Genotype Array containing approximately 750,000 genetic markers across the entire dog genome. Genome wide associations studies were run using relative serum levels of Uridine and 2-deoxy-Uridine as a continuous variable in an additive linear regression model. Relative serum levels of metabolites were determined by Metabolon.

Figure 2:
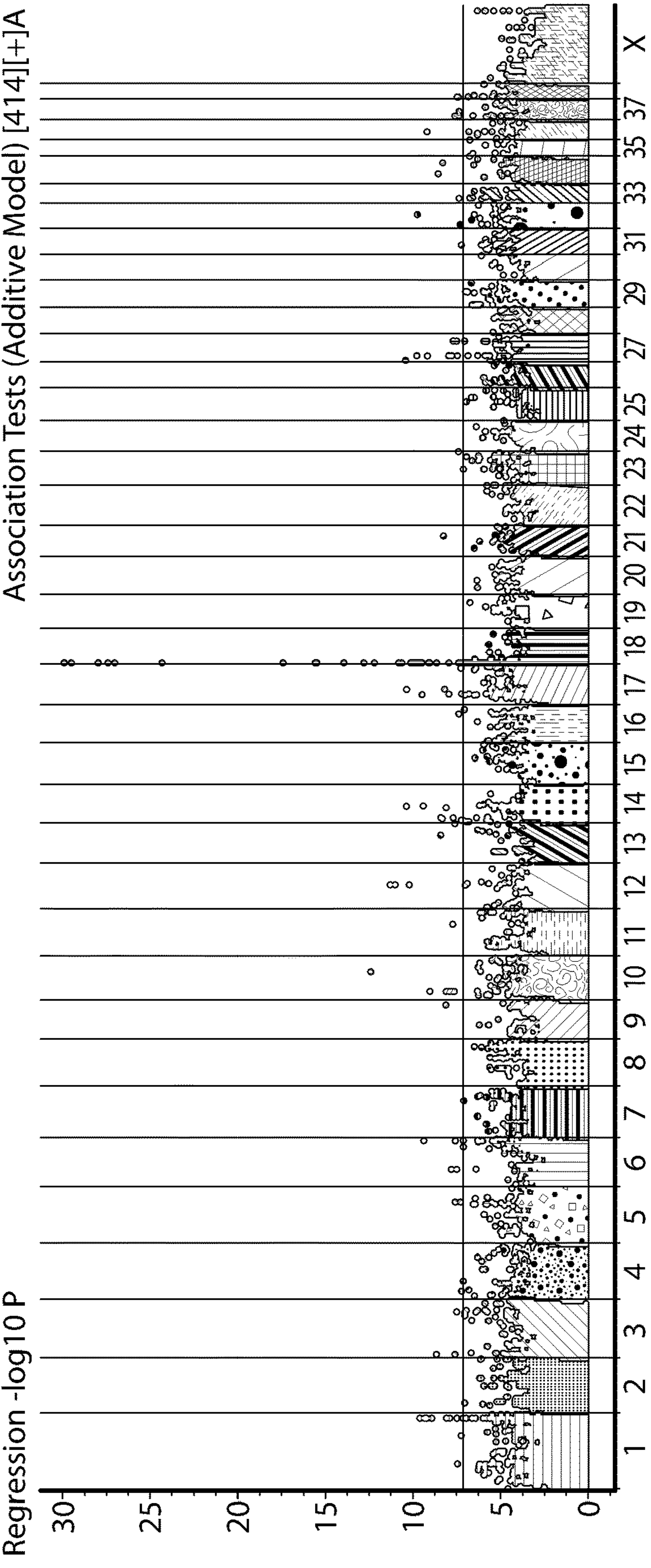
FIG. 2 shows a Uridine Manhattan plot of data from QTL analysis.
Figure 3:
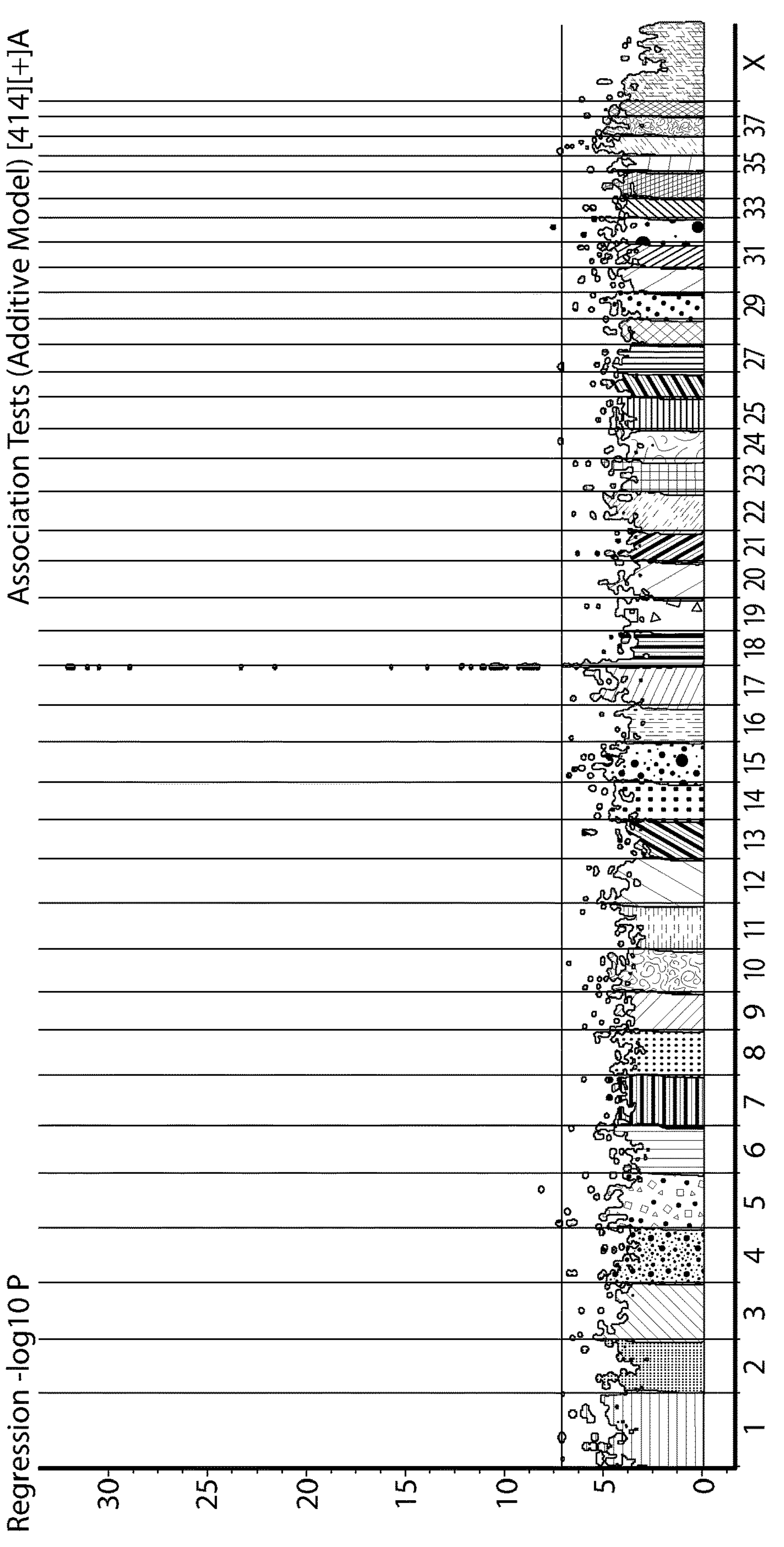
FIG. 3 shows a 2-deoxyuridine Manhattan plot of data from QTL analysis.

Using genome wide association studies (GWAS) a genetic locus has been identified that is strongly associated with serum levels of the nucleosides uridine and 2-deoxy-uridine. (FIGS. 2 and 3). The most significant genetic marker for both Uridine and 2-deoxy-Uridine is located on Chromosome 18 at base position 95375 (using the CanFam3.1 dog genome reference) with a p value of 2.99e-030 and 1.19e-032 respectively, and with a false discovery rate p value of 9.00e-025 and 7.16e-027. This Marker is a single nucleotide polymorphism with the major allele a G (allele frequency 0.59) and the minor allele an A (an allele frequency of 0.41).

This SNP is designated as marker Affx-205876096 on the Thermo Fisher Axiom HD Canine Array. The flanking DNA sequence of the SNP is disclosed herein as SEQ ID NO:1:

SEQ ID NO:1—SNP Affx-205876096 located at chr18: 95375 CanFam3.1 sequence plus 100 flanking base pairs

```
CAGTTTAAAA CTTTTGCTAA TATTTTTTGC ATAAATTGAA ATTCATAATA TTATACATTT        60

ATTATTTTGT ATCGTTTAGG TAAAACTGTG TAATTTTAAC [A/G]TTTAGCTTA GTAGTCTTAA   120

CAGAAAATTT AAAATAATCA GACTGAATTT TCTTATTTTA TAAATTTTGC TACTATTTAT       180

ACATAATTAG CATGATAATG T                                                 201
```

Figure 4:
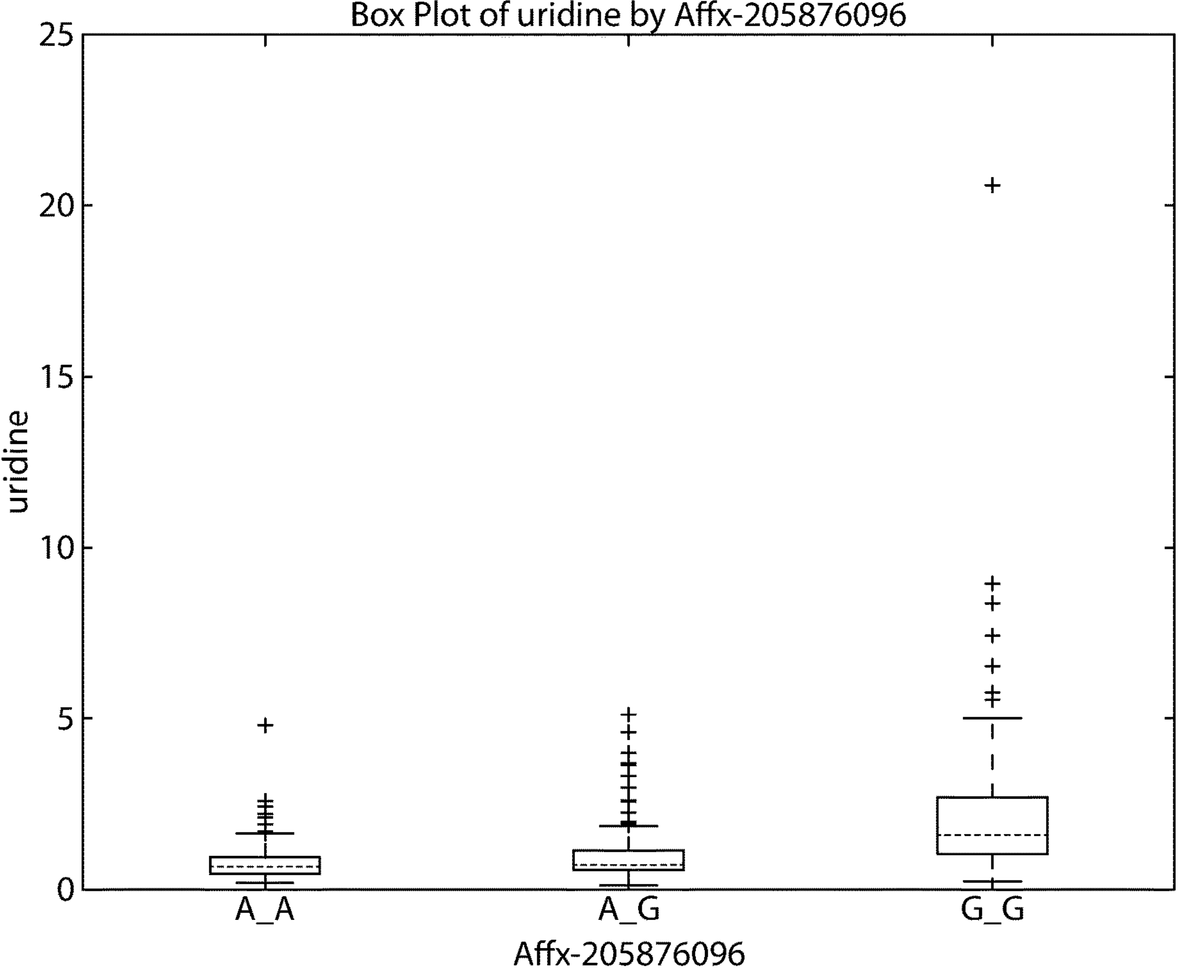
FIG. 4 shows serum levels of uridine for each genotype AA, AG, GG for SNP Affx-205876096.
Figure 5:
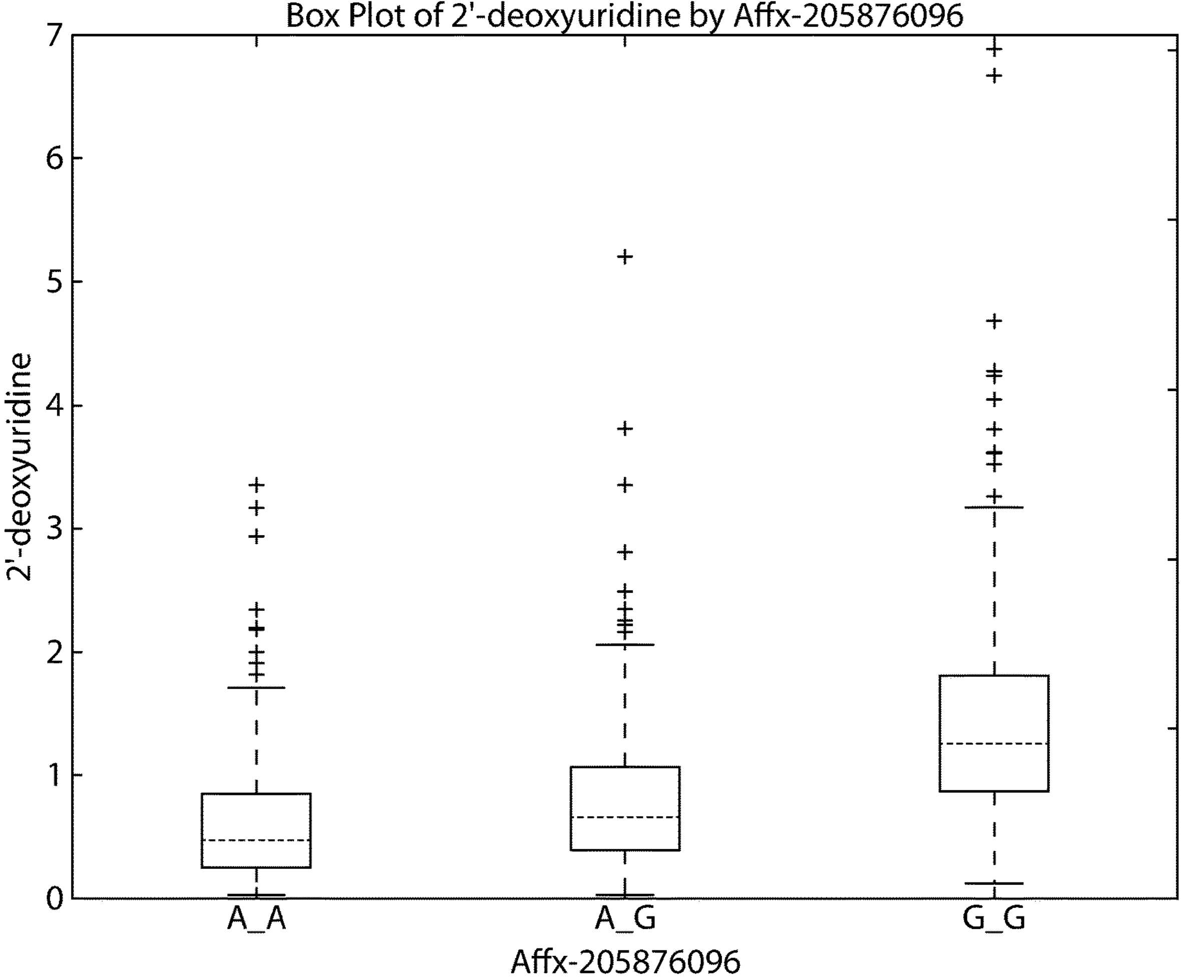
FIG. 5 shows serum levels of 2-deoxyuridine for each genotype AA, AG, GG for SNP Affx-205876096

Box plots showing the relative serum levels of Uridine and 2-deoxy-Uridine by genotype are shown in FIGS. 4 and 5.

Dogs homozygous for the G allele (~35% of Dogs in the cohort) have on average a 2-fold increase in serum Uridine and 2-deoxy-Uridine indicating that individuals with two copies of the G allele are less efficient at converting the nucleosides to the nucleic base Uracil and ribose phosphate which in turn can limit the amount of UMP generated by the pyrimidine salvage pathway. The marker Affx-205876096 is ~18 kilobases upstream of the UPP1 gene that encodes for Uridine phosphorylase, an enzyme in the nucleic base pathway.

The UPP1 gene encodes the enzyme Uridine phosphorylase (UP). Following degradation of DNA or RNA into constituent nucleosides, the nucleosides uridine or 2-deoxy uridine are processed by UP to remove the sugar from the nucleic base. UP uses phosphate and uridine (or 2-deoxyuridine) as substrates to produce uracil and ribose-1-phosphate (or deoxyribose-1-phosphate). Uracil and ribose-1-phosphate are substrates that are used by the enzyme Uridine phosphoribosyl transferase reform the nucleotide Uridine monophosphate (UMP). The. UMP then enters the normal nucleotide pathways for RNA, DNA, and other metabolic processes.

A reduction in the efficiency of UP leads to a reduced rate of converting uridine or 2-deoxy uridine to uracil and ribose-1-phosphate (or deoxyribose-1-phosphate). Uridine or 2-deoxy uridine levels increase and because there is less uracil and ribose-1-phosphate (or deoxyribose-1-phosphate, the level of UMP produced is reduced. Less UMP produced in the nucleic base salvage pathway requires more de novo nucleotide synthesis which imposes an increased energy burden.

Example 2

A nutritionally complete canine maintenance food with supplementary a therapeutic level of nucleic bases and nucleotides was prepared per Table A.

TABLE A

| Ingredient | Formula % | % Batch | Lbs/Batch | g/batch | Total lbs | Kg/batch | Total kgs |
|---|---|---|---|---|---|---|---|
| Step 1: Grain Mix | | | | | | | |
| Corn starch comm | 47.947 | 53.934 | 1051.706 | | 2103.412 | 476.964 | 953.928 |
| Chicken liver and heart | 32.000 | 35.996 | 701.912 | | 1403.825 | 318.328 | 636.655 |
| Cellulose coarse | 3.937 | 4.429 | 86.357 | | 172.714 | 39.164 | 78.328 |
| Calcium carbonate | 1.220 | 1.372 | 26.760 | | 53.521 | 12.136 | 24.272 |
| Dicalcium phosphate | 1.220 | 1.372 | 26.760 | | 53.521 | 12.136 | 24.272 |
| Gly monosterate | 0.739 | 0.831 | 16.210 | | 32.420 | 7.351 | 14.703 |
| Potassium chloride | 0.689 | 0.775 | 15.113 | | 30.226 | 6.854 | 13.708 |
| Sodium chloride iodine | 0.443 | 0.498 | 9.717 | | 19.434 | 4.407 | 8.814 |
| Methionine, dl | 0.296 | 0.333 | 6.493 | | 12.985 | 2.945 | 5.889 |
| Vitamin premix | 0.197 | 0.222 | 4.321 | | 8.642 | 1.960 | 3.919 |
| Vitamin premix | 0.118 | 0.133 | 2.588 | | 5.177 | 1.174 | 2.348 |
| Mineral premix | 0.074 | 0.083 | 1.623 | 736.132 | 3.246 | 0.736 | 1.472 |
| Taurine | 0.020 | 0.022 | 0.439 | 198.955 | 0.877 | 0.199 | 0.398 |
| Step Totals at 7.08% Moisture | | 100.000 | 1950.000 | | 3900.000 | 884.354 | 1768.707 |
| Step 2 Base Kibble | | | | | | | |
| Grain Mix | 88.900 | 97.929 | 3900.002 | | 3900.002 | 1768.709 | 1768.709 |
| Lac acid Lqd | 1.500 | 1.652 | 65.804 | | 65.804 | 29.843 | 29.843 |
| Choline chloride | 0.380 | 0.419 | 16.670 | | 16.670 | 7.560 | 7.560 |
| Beginning of Step Totals at 7.26% Moisture | | 100.000 | 3982.477 | | 3982.477 | 1806.112 | 1806.112 |
| Moisture removed 0.30%-Beginning of Step Totals at 6.96% Moisture | 1.220 | 1.372 | 26.760 | | 53.521 | 12.136 | 24.272 |
| Step 3 Finished Kibble | | | | | | | |
| Base Kibble | 90.780 | 90.754 | 423.523 | | 1270.570 | 192.074 | 576.222 |
| Soy oil crude | 4.660 | 4.673 | 21.807 | | 65.422 | 9.890 | 29.670 |
| Ck liv dig H+ | 2.000 | 2.006 | 9.359 | | 28.078 | 4.245 | 12.734 |
| CWG/Phos Acid | 1.000 | 1.003 | 4.680 | | 14.039 | 2.122 | 6.367 |
| Flav Gen#1 + CWG | 0.750 | 0.752 | 3.510 | | 10.529 | 1.592 | 4.775 |

TABLE A-continued

| Ingredient | Formula % | % Batch | Lbs/Batch | g/batch | Total lbs | Kg/batch | Total kgs |
|---|---|---|---|---|---|---|---|
| D'Tech 8P | 0.500 | 0.501 | 2.340 | | 7.020 | 1.061 | 3.183 |
| Nutrigain E | 0.160 | 0.160 | 0.749 | 339.569 | 2.246 | 0.340 | 1.019 |
| Sod tripolyphosp | 0.150 | 0.150 | 0.702 | 318.346 | 2.106 | 0.318 | 0.955 |
| End of Step Totals at 8.00% Moisture | | 100.000 | 466.670 | | 1400.010 | 211.642 | 634.925 |
| Total Ingredients required | | | | | 4111.915 | | 1864.814 |
| Amount collected | | | | | 1400.00 | | 634.921 |

This food contained 0.064% nucleotides on a dry matter basis. The food was fed to canines.

TABLE B

| Test Summary | |
|---|---|
| Test Result | Mean |
| Apparent Dry Matter Digestibility, % | 86.7 |
| Apparent Protein Digestibility, % | 85.7 |
| True Protein Digestibility, % | 92.7 |
| Apparent Fat Digestibility, % | 92.7 |
| Apparent Fiber Digestibility, % | −7.2 |
| Apparent Carbohydrate Digestibility, % | 95 |

TABLE C

| Feed Analytical Results | |
|---|---|
| Analysis | Mean |
| Diet % Moisture | 9.2 |
| Diet % Fat | 14.7 |
| Diet % Protein | 19.3 |
| Diet % NDF Fiber | 3.3 |
| Diet % Ash | 4.8 |
| Diet % Crude Fiber | 3.1 |
| Diet Kcal/lb | 2090 |

TABLE D

Quantitative Collection Method without Urine Collection

| Tattoo | Gross Energy Food AF (kcal/kg) | Food Consumed AF (g) | Gross Energy Feces AC (kcal/kg) | Feces Collected AC (g) | Protein Food AF (%) | Protein Feces AC (%) | Correction Factor (kcal/g) | ME (kcal/kg) |
|---|---|---|---|---|---|---|---|---|
| CXYAFE | 4603.52 | 1086 | 1.43612 | 409 | 19.29 | 8.3 | 1.25 | 3860.60924 |
| CXYATV | 4603.52 | 1024 | 1.42511 | 266 | 19.29 | 8.04 | 1.25 | 4018.30686 |
| L0581405 | 4603.52 | 851 | 1.87885 | 259 | 19.29 | 10.23 | 1.25 | 3829.46957 |
| 0512302 | 4603.52 | 886 | 1.41189 | 376 | 19.29 | 7.35 | 1.25 | 3803.69791 |
| CWZADV | 4603.52 | 708 | 1.70485 | 191 | 19.29 | 8.94 | 1.25 | 3932.61802 |
| CWZASX | 4603.52 | 1393 | 1.54405 | 425 | 19.29 | 9.03 | 1.25 | 3925.74793 |
| Mean | 4603.52 | 991.33 | 1.57 | 320.63 | 19.29 | 8.65 | 1.25 | 3895.06 |
| StdDev | 0 | 216.96 | 17 | 86.84 | 0 | 9 | 0 | 72.31 |
| | | | | | | | Moisture | 9.19 |
| | | | | | | | Dry Matter ME | 4289.26 |

TABLE B-continued

| Test Summary | |
|---|---|
| Test Result | Mean |
| Diet Gross Energy, kcal/kg | 4604 |
| Diet Digestible Energy, kcal/kg | 4102 |
| % NFE Calories | 49.1 |
| % Protein Calories | 18.4 |
| % Fat Calories | 32.4 |
| Initial Body Weight, kg | 12.27 |
| Final Body Weight, kg | 12.15 |
| Average Daily Intake, g | 198.23 |
| Average Stool Rating | 4.1 |
| Apparent Energy Digestibility, % | 89.1 |
| Diet Metab. Energy, kcal/kg-AAFCO Tested | 3895 |
| Apparent Vital Nutrient Digestibility, % | 94.3 |

Figure 6:
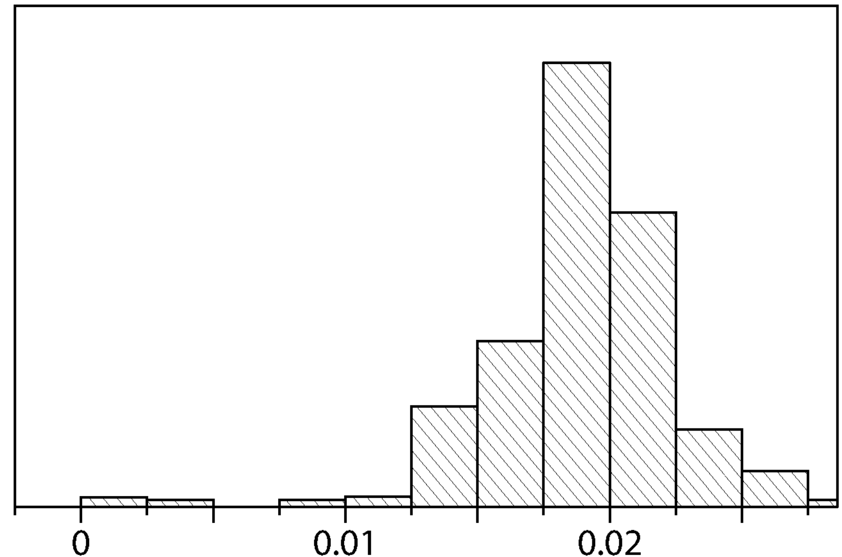
FIG. 6 shows intake of nucleotides through dietary supplementation.

Intakes, palatability and digestibility was assessed. Based on consumption, combined intake of nucleic bases and nucleotides was between 0.0001 and 0.028 g nucleotides/(KG body weight ^0.75) (FIG. 6). This level of consumption provided acceptable palatability as indicated by a standardized palatability trial with an intake ratio of 0.51.

TABLE E

| Test Summary | | | |
|---|---|---|---|
| Description | Combined | Day 1-Feeding1 | Day 2-Feeding1 |
| Number of Observations | 25 | 25 | 25 |
| Number preferring Test Diet | 11 | 12 | 16 |
| Number preferring Control Diet | 8 | 13 | 5 |
| Number with no preference | 6 | 0 | 4 |
| Percent preferring Test Diet | 44 | 48 | 64 |
| Percent Preferring Control Diet | 32 | 52 | 20 |
| Number with invalid data | 0 | 0 | 0 |
| Avg. Total Intake | 189.1 | 186 | 190.2 |

TABLE E-continued

| Test Summary | | | |
|---|---|---|---|
| Description | Combined | Day 1-Feeding1 | Day 2-Feeding1 |
| Avg. Intake of Test Diet | 95.86 | 91.84 | 99.86 |
| Avg. Intake of Control Diet | 93.24 | 98.16 | 90.32 |
| Intake Ratio | 0.506 | 0.487 | 0.529 |
| Standard Error | 0.01 | 0.0202 | 0.0169 |
| P value (2-tailed) | 0.4267 | 0.5247 | 0.1026 |
| P value (1-tailed) | 0.2134 | 0.2623 | 0.0514 |

A digestibility test was performed and showed that food provided acceptable digestibility of 94.3% Vital Nutrient digestibility. This level of nucleotides can be incorporated into a manufactured canine diet to provide supplementary nucleotides for pets who may need additional levels based on their genetic background, i.e., the GG haplotype for Affx-205876096, whereby they have deficient nucleic base salvage and have an elevated risk and higher likelihood of developing or having immune dysfunction. The food is palatable and digestible and meets canine maintenance food requirements.

Example 3

A biological sample comprising genomic DNA is obtained from a dog by collection of a cheek swab. A genetic analysis is performed to detect the GG haplotype of SNP Affx-205876096 in the sample of DNA from the dog. The detection of the GG haplotype of SNP Affx-205876096 indicates that the dog has a defect and deficiency in nucleic base salvage. The dog, which is identified as not having any symptoms of immune dysfunction at the time of testing, is identified as having an elevated risk and higher likelihood of developing.

The dog is fed a nutritionally complete diet is a nutritionally complete and balanced dog food that comprised a therapeutic level of nucleotides wherein the food comprises 0.064% nucleotides on a dry matter basis.

Example 4

A biological sample comprising genomic DNA is obtained from a dog by collection of a cheek swab. A genetic analysis is performed to detect the GG haplotype of SNP Affx-205876096 in the sample of DNA from the dog. The detection of the GG haplotype of SNP Affx-205876096 indicates that the dog has a defect and deficiency in nucleic base salvage. The dog is identified as being diagnosed with or suspected of having immune dysfunction at the time of testing.

The dog is fed a nutritionally complete diet is a nutritionally complete and balanced dog food that comprised a therapeutic level of nucleotides wherein the food comprises 0.064% nucleotides on a dry matter basis.

Example 5

A daily diet that comprises therapeutic levels of nucleotides provides significant benefits to dogs identified as having the GG haplotype of SNP Affx-205876096. In some embodiments, methods may comprise feeding a dog identified as having the GG haplotype of SNP Affx-205876096 a daily diet that comprises a therapeutic level of nucleotides. In some embodiments, methods may comprise feeding a dog having the GG haplotype of SNP Affx-205876096 but no symptoms or indicators of active immune dysfunction a daily diet that comprises therapeutic amount nucleotides. In some embodiments, methods may comprise feeding a dog that has been diagnosed with or suspected of having immune dysfunction and identified as having the GG haplotype of SNP Affx-205876096 a daily diet that comprises a therapeutic amount of nucleotides. In some embodiments, methods may comprise measuring serum uridine and deoxy-uridine in a canine and comparing the measured level to a reference standard value to identify the canine as having elevated uridine and deoxy-uridine and feeding a dog a daily diet that comprises a therapeutic amount of nucleotides. The reference standard value may be a positive reference standard that corresponds to levels serum uridine and deoxy-uridine deemed to be an elevated level for a dog of comparable size, weight, age, breed inter alia. The reference standard value may be a negative reference standard that corresponds to levels serum uridine and deoxy-uridine deemed to be a normal level for a dog of comparable size, weight, age, breed inter alia.

Example 6

The following composition is based upon total nutrition to be provided per day.

In some embodiments, based on the total weight of the composition on a dry matter basis, the compositions comprise chicken in an amount from 5% to 25%, egg protein in an amount from 4% to 15%, corn gluten meal in an amount from 6% to 20%, vegetables thereof, in an amount from 0.5% to 2%, fruit in an amount from 0.5% to 2%, and a carbohydrate selected from millet, brewers rice, oat groats, and combinations thereof in an amount of 5% to 50% based on the total weight of the composition on a dry matter basis.

In some embodiments based on the total weight of the composition on a dry matter basis, the amount of nucleotides is equal to 0.055-0.075%. In some embodiments based on the total weight of the composition on a dry matter basis, the amount of nucleotides is equal to 0.060-0.070%. In some embodiments based on the total weight of the composition on a dry matter basis, the amount of nucleotides is equal to 0.062-0.068%. In some embodiments based on the total weight of the composition on a dry matter basis, the amount of nucleotides is equal to 0.063-0.065%. In some embodiments based on the total weight of the composition on a dry matter basis, the amount of nucleotides is equal to about 0.064%.

In certain embodiments, compositions may comprise chicken in an amount of 5%, 7.5%, 10%, 12.5%, 15%, 17.5%, 20%, 22.5% or 25% based on the total weight of the composition on a dry matter basis. In certain embodiments, compositions may comprise egg protein in an amount of 4%, 5%, 6%, 7%, 8%, 9%, 10%, 11%, 12%, 13%, 14% or 15% based on the total weight of the composition on a dry matter basis. In certain embodiments, compositions may comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In certain embodiments, compositions may comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise a fruit source in an amount of 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% based on the total weight of the composition on a dry matter basis. In certain embodiments, compositions may comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

Example 7

Table F describes certain embodiments having proportion of the composition (% of dry weight of component composition)

Table F describes certain embodiments having proportion of the composition (% of dry weight of component composition) that includes a therapeutic level of nucleotides such as 0.055-0.075% based on dry weight. In some embodiments, the therapeutic level of nucleotides is 0.064%

TABLE F

| | |
|---|---|
| Protein | from about 5% to about 70%, or from about 10% to about 70%, or from about 10% to about 60% |
| Carbohydrate (preferably a nitrogen-free or essentially nitrogen-free extract) | from about 0% to about 50%, or from about 5% to about 45% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins, and minerals) | from about 0% to about 15%, or from about 2% to about 8% |
| Nucleotides | from about 0.055% to about 0.075%, or from about 0.060% to about 0.070%, or from about 0.062% to about 0.068% |

Example 8

Table G describes certain embodiments having proportion of the composition (% of dry weight of component composition).

TABLE G

| Description | Content Range (w/w %) |
|---|---|
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |
| Nucleotides | from about 0.055% to about 0.075%, or from about 0.060% to about 0.070%, or from about 0.062% to about 0.068%; |

Example 9

Table H describes certain embodiments having proportion of the composition (% of dry weight of component composition.

TABLE H

| Ingredient | w/w % |
|---|---|
| Chicken, livers, hydrolyzed, dry | 36.79 |
| Corn, starch, common canning | 32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | 4.00 |
| Cellulose, coarse | 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | 2.50 |
| OatWell ® 22 oat bran | 3.00 |
| Pecan Fiber | 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |
| Nucleotides | from about 0.055% to about 0.075%, or from about 0.060% to about 0.070%, or from about 0.062% to about 0.068%; |

Example 10

Table I describes certain embodiments having proportion of the composition.

TABLE I

| Ingredient | w/w % |
|---|---|
| Rice, brewers | 25.00 |
| Pea, protein concentrate | 10.00 |
| Chicken Dried 10% Ash | 8.00 |
| Chicken, ground, fresh | 7.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |

TABLE I-continued

| Ingredient | w/w % |
|---|---|
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flav Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |
| Mineral, premix, 2305 | 0.04 |
| Oat Fiber, Fruit, Vegetable blend | 0.04 |
| Dicalcium phosphate | 0.04 |
| Nucleotides | about 0.064% |

Example 11

Table J describes ingredients used in certain embodiments having proportion of the composition (% of dry matter weight of component composition).

TABLE J

| Ingredient | w/w % |
|---|---|
| Rice, Brewers | — |
| Chicken Meal | 7.00 |
| Pea, protein concentrate | 8.00 |
| Cellulose, coarse | 4.00 |
| Chicken Dried 10% Ash | 6.00 |
| Barley, pearled, cracked | 20.00 |
| Chicken, ground, fresh | 8.00 |
| Flax, seed, whole | 2.00 |
| Coconut oil preserved | 4.00 |
| Chicken, liver, digest, optimizor LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |
| Nucleotides | about 0.064 |

Example 12

Table K describes ingredients used in certain embodiments having proportion of the composition (% of dry matter weight of component composition).

TABLE K

| Ingredient | w/w % | w/w % |
|---|---|---|
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizer LDPE H | 2.00 | 2.00 |
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flav Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | 7.00 | — |
| Flax seed whole brown | 3.00 | — |
| Beet pulp, ground, fine | 2.50 | — |
| Cranberry pomace | 1.00 | — |
| Nucleotides | 0.064 | 0.064 |

Example 13

Table L describes ingredients used in certain embodiments having proportion of the composition (% of dry matter weight of component composition).

TABLE L

| Ingredient | w/w % | w/w % |
|---|---|---|
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | 26.00 | 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |
| Nucleotides | 0.064 | 0.064 |

Example 14

Table M describes ingredients used in certain embodiments having proportion of the composition (% of dry matter weight of component composition).

TABLE M

| Ingredient | w/w % | w/w % | w/w % | w/w % |
|---|---|---|---|---|
| Protein | 19.7 | 24.7 | 24.8 | 24.8 |
| Fat | 26.13 | 22.164 | 27.5 | 26.6 |
| Carbohydrate | 53.8 | 51.0 | 46.3 | 27.6 |
| Crude Fiber | 0.306 | 2.436 | 1.336 | 20.936 |
| Nucleotides | 0.064 | 0.064 | 0.064 | 0.064 |

The invention claimed is:

1. A method of preventing, delaying onset of or reducing severity of symptoms of immune dysfunction in a dog comprising identifying the dog as being at an increased risk or likelihood of developing immune dysfunction according to a method of identifying comprising analyzing a biological sample obtained from the dog for presence of 2 copies of major allele G for single nucleotide polymorphism Affx-205876096 in the dog; and identifying that the dog has the increased likelihood or risk of developing immune dysfunction by the presence of 2 copies of major allele G for single nucleotide polymorphism Affx-205876096, and administering to the dog a complete nutritional diet that comprises a therapeutic level of nucleotides, wherein the complete nutritional diet is a complete and balanced nutritional dog food that comprises 0.055-0.075% nucleotides on a dry matter basis when the dog is identified as having the increased likelihood or risk of developing immune dysfunction.

2. A method of treating a dog diagnosed with or suspected of having immune dysfunction comprising:

identifying the dog as a dog diagnosed with or suspected of having immune dysfunction;

identifying the dog as having a defect or deficiency in nucleic base salvage by analyzing a biological sample obtained from the dog for the presence of 2 copies of major allele G for single nucleotide polymorphism Affx-205876096; and identifying the dog as having the defect or deficiency in nucleic base salvage by the presence of 2 copies of major allele G for single nucleotide polymorphism Affx-205876096, and administering to the dog a complete nutritional diet that comprises a therapeutic level of nucleotides, wherein the complete nutritional diet is a complete and balanced nutritional dog food that comprises 0.055-0.075% nucleotides on a dry matter basis when the dog is identified as diagnosed with or suspected of having the immune dysfunction or identified as having the defect or deficiency in nucleic base salvage.

3. The method of claim 2 wherein the complete and balanced nutritional dog food comprises 0.064% nucleotides on a dry matter basis.

4. The method of claim 1, wherein the analyzing comprises performing at least one nucleic acid analysis technique selected from: DNA sequencing, restriction enzyme digest, polymerase chain reaction (PCR), hybridization, real-time PCR, reverse transcriptase PCR, or ligase chain reaction.

5. The method of claim 1, wherein the analyzing comprises performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping.

6. The method of claim 1, wherein the analyzing comprises performing at least one nucleic acid analysis technique selected from: hybridization-based methods, enzyme-based methods, post-amplification methods based on physical properties of DNA, and sequencing methods.

7. The method of claim 1, wherein the analyzing comprises performing at least one nucleic acid analysis technique selected from: hybridization-based methods selected from the group consisting of dynamic allele-specific hybridization, molecular beacon methods and SNP microarrays;

enzyme-based methods selected from the group consisting of restriction fragment length polymorphism (RFLP), PCR-based methods, Flap endonuclease, primer extension methods, 5'-nuclease and oligonucleotide ligation assay; and post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, and surveyor nuclease assay; and sequencing methods.

8. The method of claim 1 wherein the complete and balanced nutritional dog food comprises 0.064% nucleotides on a dry matter basis.

9. The method of claim 1 comprising the additional step of measuring the serum level of uridine and/or deoxyuridine or both in the dog and comparing the level measured to a standard indicative of a serum level in dogs with a normal nucleic base salvage process.

10. The method of claim 1, wherein the biological sample is a genomic DNA sample.

11. The method of claim 1, wherein the sample is obtained from blood, saliva, follicle root, nasal swab or oral swab of the dog.

12. The method of claim 2 comprising the additional step of measuring the serum level of uridine and/or deoxyuridine or both in the dog and comparing the level measured to a standard indicative of a serum level in dogs with a normal nucleic base salvage process.

13. The method of claim 2, wherein the biological sample is a genomic DNA sample.

14. The method of claim 2, wherein the sample is obtained from blood, saliva, follicle root, nasal swab or oral swab of the dog.

15. The method of claim 2, wherein the analyzing comprises performing at least one nucleic acid analysis technique selected from: hybridization-based methods, enzyme-based methods, post-amplification methods based on physical properties of DNA, and sequencing methods.

16. The method of claim 2, wherein the analyzing comprises performing at least one nucleic acid analysis technique selected from: hybridization-based methods selected from the group consisting of dynamic allele-specific hybridization, molecular beacon methods and SNP microarrays; enzyme-based methods selected from the group consisting of restriction fragment length polymorphism (RFLP), PCR-based methods, Flap endonuclease, primer extension methods, 5'-nuclease and oligonucleotide ligation assay; and post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, and surveyor nuclease assay; and sequencing methods.

* * * * *